United States Patent [19]
Eloy

[11] 4,330,208
[45] May 18, 1982

[54] PROCESS AND APPARATUS FOR REGULATING THE IMPACT OF A LIGHT BEAM ON A TARGET

[75] Inventor: Jean-François Eloy, Saint Ismier, France

[73] Assignee: COMMISSARIAT a l'Energie Atomique, Paris, France

[21] Appl. No.: 138,712

[22] Filed: Apr. 9, 1980

[30] Foreign Application Priority Data

Apr. 18, 1979 [FR] France .................................. 79 09763

[51] Int. Cl.³ .................... G01N 21/63; B23K 26/02; B23K 26/06
[52] U.S. Cl. .......................... 356/318; 219/121 LY; 219/121 LZ; 219/121 LR; 250/288; 250/491; 356/399
[58] Field of Search ................ 365/301, 317, 318, 399; 250/288, 423 P, 425, 491; 350/294; 219/121 LP, 121 LY, 121 LZ, 121 LS, 121 LR, 121 LU, 121 LM

[56] References Cited

U.S. PATENT DOCUMENTS 3,782,823 1/1974 Kantorski et al. .................. 356/318
3,892,488 7/1975 Edmonds ..................... 219/121 LY

OTHER PUBLICATIONS

"Korall-I, A Laser for Atomic Spectral Analysis", J. of Applied Spectroscopy, Vyzhelevskii et al., vol. 23#3, pp. 1260-1264. Sep. 1975.

Primary Examiner—Vincent P. McGraw
Attorney, Agent, or Firm—Pearne, Gordon, Sessions, McCoy & Granger

[57] ABSTRACT

Process and apparatus for regulating the impact on a target of a light beam emitted by a source. The position and dimension of the impact are regulated by respectively using two beams, whose optical paths are coaxial.

The apparatus comprises a target support and means for displacing it in its plane, means for focusing the light beam of the source on the target, means for regulating said focusing means, means for emitting a regulating light beam in the direction of the target, the location and dimensions of the impact of said regulating beam on the target corresponding to the predetermined location and dimensions of the impact of the light beam of the source, as well as optical visual display means for locating and regulating the dimension of the impact of the regulating beam, wherein the means for emitting the regulating beam and the visual display means for the impact position of the regulating beam on the target are independent of the means for focusing the light beam of the source, the optical paths of the light beam of the source and the visual display means for the impact position being coaxial and the optical paths for the visual display means for regulating the impact dimensions and the light beam of the source partly coincide.

10 Claims, 1 Drawing Figure

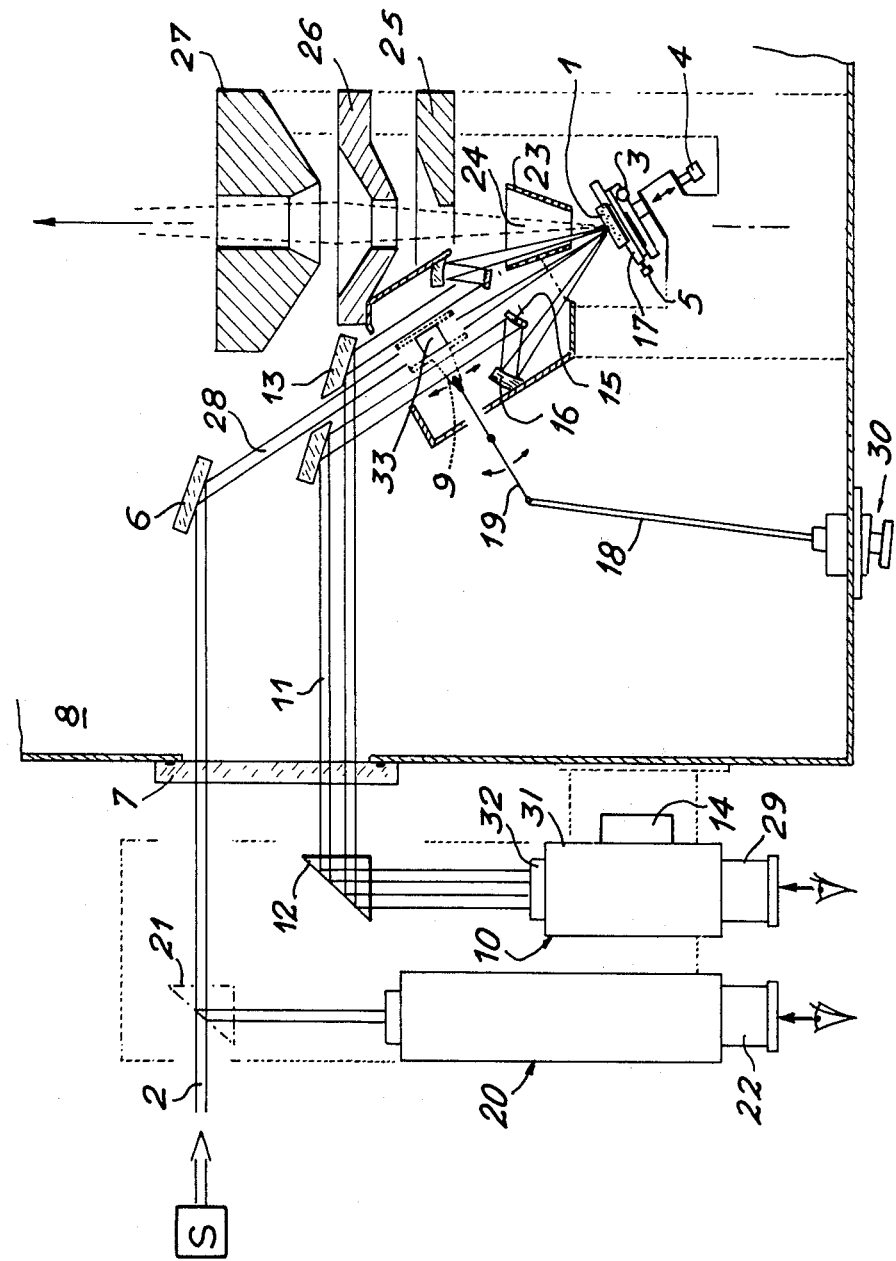

PROCESS AND APPARATUS FOR REGULATING THE IMPACT OF A LIGHT BEAM ON A TARGET

BACKGROUND OF THE INVENTION

The present invention relates to a process and to an apparatus for regulating the impact of a light beam, particularly a monochromatic light beam on a target and which is emitted by a source and particularly a laser source.

Particularly in laser spectrometry, this process and this apparatus make it possible to accurately regulate the position and dimension of the impact of a monochromatic laser beam on a target. It also makes it possible to maintain the impact of the laser beam on the target in a fixed position in space.

It is known that in laser spectrometry, it is necessary to accurately determine the position on the target and the dimension of the impact of a laser beam bombarding the said target in order to mark the analysed point and control the dimensions of the volume of material vapourized by this bombardment and thus control the emission of the particles resulting from this impact. In addition, it must be possible to carry out this regulation for several wavelengths, because the results of the spectrometric analysis resulting from the impact of the laser beam on the target are linked with the wavelength of the light of the bombardment beam.

In the special case of laser mass spectrometry this regulation must also make it possible for the ion source which extracts the ions transmitted into the spectrometer from the laser plasma to operate continuously under good conditions. This requires an invariable relative position of the laser impact and the ionic optics of the ion source of the spectrometer.

Laser spectrometry consists of producing microplasmas from a solid surface, locally excited by a focused laser light beam. The thus produced microplasmas then are analysed by means of a spectrometer, particularly a mass spectrometer. The laser beam focusing device generally comprises an optical lens with weak magnification, whose focal point position is dependent on the wavelength of the monochromatic laser light beam. Thus, for example said focal length is longer for an infrared laser light ($\lambda = 0.6943\mu$) than for an ultraviolet laser light ($\lambda = 0.347\mu$). Microplasmas can be produced by focusing laser light either by the incidence of the laser beam on the surface of a target bringing about the emission of a microplasma on the same side of this surface as the laser beam (by reflection) or by incidence of the beam on the surface of a thin target, which brings about the emission of a microplasma on the other face of the target (by transmission). The energy spectrum of the emitted particles is dependent on the position on the focal point of the laser light beam relative to the surface to be investigated. For the emission of microplasmas to be effective by reflection, it is necessary for the focusing point of the laser beam to be slightly in front of the surface and not on it.

It is known to utilize a visible light illumination of the object to carry out the focusing of the focusing means of the laser beam. This focusing is brought about by optical means for which the path of the visible light, used for regulating the focusing is identical to that of the laser beam. This has the serious disadvantage of making uncertain an optimum regulation of the focusing position of the monochromatic laser bean used (e.g. ultraviolet or infrared light). Thus, as has been stated hereinbefore, the focusing position is dependent on the wavelength of the light traversing the focusing means and as a result it is not possible to correctly regulate in white light the focusing position to be obtained in monochromatic laser light. The dimensions of the volume of the material which will be vapourized cannot be predetermined.

No presently known process or apparatus makes it possible to simultaneously solve the problems of precisely locating the point of impact of the laser beam on the surface of the targets under investigation and the problem of regulating the focusing position of the laser beam. Solving these two problems would make it possible to determine beforehand the optimum interaction conditions between the laser beam and the material under investigation.

The only problem which has been solved at present is that of regulating the position of the impact of the laser beam on the target. This can be carried out very accurately when the optical paths of the bombardment laser beam and of the white light beam used in optical impact location means coincide.

Among the presently known devices using this locating method developed by light spectroscopy, one of them comprises a lens for focusing the laser beam which has a double spherical mirror for deviating the bombardment laser beam and the locating white light beam. By means of a telescopic prism system placed on the optical axis of the lens, the laser beam and the white light beam have the same optical axes level with the incidence on the object and as a result the impact point of the laser beam is located in a clearly defined manner. However, as the wavelengths of the laser beam light and white light differ, the device does not make it possible to accurately determine the focusing position of the laser beam and consequently the dimensions of the impact of said beam on the target. Thus, as the focusing distance differs between monochromatic light and white light, the dimensions of the impact obtained in monochromatic light cannot be foreseen. In this device, the target is carried by a support which can only be moved in a plane perpendicular to the direction of the laser beam. Another disadvantage of the known devices is that when the thickness of the target to be analysed varies, the position of the plasma cluster created by laser impact varies. Although this is not prejudicial in light spectroscopy in mass spectroscopy, said position is no longer continuously adapted to the satisfactory operation of the ion source of the mass spectrometer. The diameter of the impact of the beam on the target is predetermined as a function of the wavelength of the laser beam by defocusing and the use of a series of diaphragms having different diameters connected to the focusing lens. This system is not very suitable for mass spectrometry because it is difficult to fit the diaphragms. Thus, the lens is then placed within a vacuum enclosure, which cannot be opened during the experiment. This is very prejudicial when the experiment requires the successive use of monochromatic laser beams of different wavelengths. Moreover, this device does not make it possible to obtain a definite and distinct sighting of the sample during the experiment, because the laser beams and white light beams used for sighting and observation coincide over a large part of their paths.

BRIEF SUMMARY OF THE INVENTION

The object of the present invention is to obviate these disadvantages and in particular to provide an apparatus and a process for regulating the impact on a target of a monochromatic light beam emitted by a laser source and making it possible to simultaneously ensure a satisfactory location of the said impact and the predetermination of the dimensions thereof. Moreover, said apparatus makes it possible to study samples of different wavelengths. It also permits a satisfactory observation of the impact point of the beam, on the target during experiments. These results are obtained by means of coaxial, but non-coinciding optical paths for the laser beam and for the observation white light beam.

The invention relates to a process for regulating the impact of a light beam emitted by a source on a target, wherein it comprises regulating the position and dimension of the impact by respectively using two beams whose optical paths are coaxial.

According to another feature of the process, as the light beam of the source is monochromatic the position and dimensions of the impact are regulated in white light, the optical path of the location regulating beam being coaxial to the optical path of the beam of the source and the optical path of the impact dimension regulating beam partially coinciding with the optical path of the beam of the source.

According to another feature of this process a correction lens making it possible to obtain in white light the predetermined dimensions of the desired impact in the selected monochromatic light is interposed on the optical path of the dimension regulating beam.

The invention also relates to an apparatus for regulating the impact of a light beam emitted by a source on a target and which comprises a target support and means for moving it in its plane, means for focusing the light beam of the source on the target, means for regulating said focusing means, means for emitting a regulating light beam in the direction of the target, the location and dimension of the impact of said regulating beam on the target corresponding to the predetermined location and dimensions of the impact of the light beam of the source, as well as optical visual display means for locating and regulating the dimension of the impact of the regulating beam, wherein the means for emitting the regulating beam and the visual display means for the impact position of the regulating beam on the target are independent of the means for focusing the light beam of the source, the optical paths of the light beam of the source and the visual display means for the impact position being coaxial and the optical paths for the visual display means for regulating the impact dimensions and the light beam of the source partly coincide.

According to another feature of the apparatus the means for emitting the regulating beam and the visual display means of the impact of this beam are fixed and associated with means for moving the target support parallel to the beam of the source and to the regulating beam.

According to another feature of the apparatus the source is a monochromatic light source and the regulating beam a white light beam.

According to another feature the means for the visual display of the impact dimension of the regulating beam on the target are associated with focusing means for regulating in white light the impact dimension on the target.

According to another feature the means for the visual display of the impact dimension are associated with a correction lens making it possible to obtain in white light and due to means for regulating the focusing means the predetermined dimension of the desired impact in the selected monochromatic light.

According to another feature the means for the visual display of the impact position of the regulating beam on the target are constituted by a first sight associated with an annular objective, a light beam source being incorporated into the said sight for producing the regulating beam, the means for the visual display of the impact dimension being constituted by a second sight receiving the impact of the image of the regulating beam through focusing means, the eyepiece of the second sight being provided with the aforementioned correction lens.

DESCRIPTION OF THE DRAWING AND PREFERRED EMBODIMENTS

The invention is described in greater detail hereinafter relative to non-limitative embodiments and the attached drawing, wherein it is possible to see in part sectional form an apparatus according to the invention.

The apparatus according to the invention shown in the drawing makes it possible to regulate the impact on a target 1 of a monochromatic light beam emitted by a laser source S. This target is placed on a support 17 which can be moved in three perpendicular directions by displacement means constituted by micrometer screws 3, 4, 5. The laser beam 2 is deviated by a mirror 6 after passing through the transparent shield window 7 of a vacuum enclosure 8 in which are placed the target 1 to be investigated, as well as the various optical and electrical means which will be described in greater detail hereinafter. Laser beam 2 is deviated by mirror 6 in such a way that the axis of this beam is perpendicular to the surface of target 1. The apparatus also comprises focusing means 9 for the laser beam and means 10 making it possible to emit in the direction of the target and through the shield window 7 an annular regulating light beam 11. This regulating beam is deviated by prism 12 and by inclined mirror 13 which has an opening for the passage of the laser beam. The regulating light beam is a white light beam and, as will be shown hereinafter, the location and impact dimension of this light beam on the target corresponds to the predetermined location and dimension of the impact of the laser beam on said target. The means for emitting the regulating light beam and visual display of the impact position of the light beam on the target are constituted by a first sight 31, whose objective is shown at 32 and by a light source 14, incorporated into said sight for producing the regulating light beam 11. This sight is associated with an annular lens or objective incorporating two annular spherical mirrors 15, 16, which permit the passage of the laser beam, whilst permitting the annular white light beam 11 to be focused on the axis of laser beam 2. Thus, the laser beam and the regulating light beam for locating the impact on target 1 are partially coaxial. The location of the impact point of the laser beam on the target is brought about on the basis of the location of the impact point of the white light beam on said target, due to the coaxiality of said beams. The focusing means 9 of the laser beam are constituted by a lens 33. Their position on the axis of the beam is regulatable by means of a lever system 18, 19 making it possible to translate lens 9 along the axis of the laser beam. This displacement of the lens makes it possible to regulate the impact dimension of the laser beam on the target on the basis of the impact dimension of the white light beam on said target. This dimension regulation is visually controlled by visual display means for the impact dimension, constituted by a second sight 20 making it possible to regulate the impact diameter of the laser beam on the target, due to the movement of support 17 controlled by displacement means 4. Due to sighting in white light in sight 31, this movement makes it possible to place the target at the focal point of annular objective 15, 16. The position of this focal point is adapted to the ion source of the mass spectrometer. The regulation of the dimension of this impact is ensured by a displacement of the focusing lens 33 controlled by levers 18, 19 from micrometer screw 30 positioned externally of enclosure 8. The optical paths of the laser beam and the beam from the second sight partly coincide and traverse the focusing lens 9. The optical paths of the beams reaching the first and second sights permitting the location of the impact and regulation of its dimension are coaxial. The second sight 20 receives the image of the impact on the target of the regulating light beam through the focusing lens 33 and a telescopic prism 21. The eyepiece 22 of the second sight 20 incorporates a convergent or divergent lens (not shown) making it possible to obtain in white light an image of the impact of the same size as that of the impact with a monochromatic light beam of the same wavelength as that of the beam emitted by the bombardment laser. To this end and in order to facilitate regulations when the target must be bombarded by successive beams of different wavelengths, the correction lenses of eyepiece 22 can be mounted on a not shown barrel making it possible to position in front of the eyepiece the lens corresponding to the wavelength of the monochromatic light emitted by the laser. Finally, laser source S comprises a laser emitting the monochromatic light beam, for processing or bombarding the target and another "alignment" laser, which emits a visible light beam which spatially coincides with the processing beam. The beam emitted by the alignment laser makes it possible to control the correct location of the impact of the processing laser beam on the target, when all the settings have been made. As is apparent from the drawing, the focusing lens is protected against possible projections of particles during the impact of the bombardment beam on the target by the annular objective 15, 16, which is itself protected from these projections. Thus, the active face of mirror 15 is opposite to the target, whilst the active face of mirror 16 is remote from the target and is partly protected by mirror 15.

As the apparatus according to the invention is mainly intended for spectrometry in the vicinity of the target is provided an expansion chamber constituted by a conical tube 23 making it possible to collect particles, such as ions, contained in the microplasma particle beam 24. This beam is then concentrated and accelerated by means of electrodes 25, 26, 27, raised for example to positive potentials compared with a reference potential. Reference potential can be the potential of the enclosure 8. The thus concentrated and accelerated particles are then directed towards a not shown spectrometer.

The apparatus described hereinbefore functions as follows. The light source of the first eyepiece 10 is switched on when the bombardment laser is switched off. The impact position on the target, viewed through the first eyepiece, is then regulated by a displacement of the support 17 in a plane perpendicular to the axis of beam 28 of the alignment laser. It is thus possible to locate the impact position of the bombardment laser beam on the target. To compensate thickness variations of the target and obtain a laser plasma in an invariable position with respect to the ion source, it is optionally possible to move the target support in a direction parallel to the axis of the alignment laser beam in such a way that the annular white light beam of the sight converges on the target surface. Lens 33 is then moved in a direction parallel to the laser beam axis so as to distinguish in the eyepiece 22 of the second sight 20 a distinct and clearly defined image of the surface of the target illuminated with white light by the beam emitted by the first eyepiece. The regulation of the dimension of the future laser impact is ensured after inserting the monochromatic light correction lens in the eyepiece 22 of the second sight 20 by a displacement in translation of lens 33 under the control of levers 18, 19 operated by the micrometer screw 30 (obviously the dimension regulation can be directly carried out with the selected correction lens). Finally, it may be necessary to move the support 17 very slightly in a plane perpendicular to the laser beam axis in such a way as to adjust the impact image of the alignment beam, whose optical path coincides with that of the bombardment laser with the reticle of eyepiece 29 of the first sight 31. To this end, the alignment laser is switched on and this latter check makes it possible to modify the setting of support 17 so as to be able to control the location of the impact prior to the experiment. Following these setting operations, the apparatus is ready to carry out the spectrometric measurements. The alignment laser is switched off and the bombardment laser switched on. As a result of these settings, it is certain that it will be possible to obtain on that target, an impact of the beam of the bombardment laser, whose position and dimension are predetermined. Whereas the alignment laser operates in a continuous manner invisible light, the bombardment laser operates in a pulsating manner. In addition, a laser light attenuator can be placed on the path of the bombardment beam so as to predetermine the thickness of the target material which has to be sampled.

The apparatus according to the invention described hereinbefore makes it possible to achieve the aforementioned objectives and in particular a high degree of accuracy in the location and focusing of the bombardment beam. It also permits the continuous observation of the impact zone during bombardment, it prevents the interference caused in the prior art apparatus by the expansion of the microplasms in the vicinity of the focusing lens and the sighting objective. Finally, as a result of a preferred positioning of the two lenses, it prevents the atomization of the material emitted during the bombardment on the focusing lens and the sighting objective.

Although the invention has been described and represented with respect to specific embodiments, it is not limited thereto and various modifications can be made within the scope of the invention.

What is claimed is:

1. A process for regulating the impact of a light beam emitted by a source on a target, wherein it comprises regulating the position and dimensions of the impact by respectively using two beams whose optical paths are coaxial, the light beam of the source being monochromatic, the position and dimensions of the impact being regulated in white light, the optical path of the location regulating beam being coaxial to the optical path of the beam of the source, and the optical path of the impact dimension regulating beam partially coinciding with the optical path of the beam of the source.

2. A regulating process according to claim 1, wherein a correction lens making it possible to obtain in white light the predetermined dimensions of the desired impact in the selected monochromatic light is interposed on the optical path of the dimension regulating beam.

3. An apparatus for regulating the impact of a light beam emitted by a source on a target and which comprises a target support and means for moving it in its plane, means for focusing the light beam of the source on the target, means for regulating said focusing means, means for emitting a regulating light beam in the direction of the target, the location and dimensions of the impact of said regulating beam on the target corresponding to the predetermined location and dimensions of the impact of the light beam of the source, as well as optical visual display means for locating and regulating the dimension of the impact of the regulating beam, wherein the means for emitting the regulating beam and the visual display means for the impact position of the regulating beam on the target are independent of the means for focusing the light beam of the source, the optical paths of the light beam of the source and the visual display means for the impact position being coaxial and the optical paths for the visual display means for regulating the impact dimensions and the light beam of the source partly coincide.

4. A regulating apparatus according to claim 3, wherein the means for emitting the regulating beam and the visual display means of the impact of this beam are fixed and associated with means for moving the target support parallel to the beam of the source and to the regulating beam.

5. A regulating apparatus according to claim 3 or 4, wherein the source is a monochromatic light source and the regulating beam a white light beam.

6. A regulating apparatus according to claim 5, wherein the means for the visual display of the impact dimension of the regulating beam on the target are associated with focusing means for regulating in white light the impact dimension on the target.

7. A regulating apparatus according to claim 6, wherein the means for the visual display of the impact dimension are associated with a correction lens making it possible to obtain in white light and due to means for regulating the focusing means the predetermined dimension of the desired impact in the selected monochromatic light.

8. A regulating apparatus according to claim 7, wherein the means for the visual display of the impact position of the regulating beam on the target are constituted by a first sight associated with an annular objective, a light beam source being incorporated into the said sight for producing the regulating beam, the means for the visual display of the impact dimension being constituted by a second sight receiving the impact of the image of the regulating beam through focusing means, the eyepiece of the second sight being provided with the aforementioned correction lens.

9. An apparatus according to claim 8, wherein the annular objective comprises a system of two annular spherical mirrors arranged coaxially on the path of the regulating beam so as to focus said beam on the target.

10. A regulating apparatus according to claim 9, wherein the light source is a laser source incorporating on the one hand a laser emitting a target processing monochromatic light beam and on the other an alignment laser emitting a visible light beam which spatially coincides with the processing beam, the impact on the target of the alignment laser beam having to coincide with a reticle of the first sight.

* * * * *